(12) United States Patent
Gobrecht et al.

(10) Patent No.: US 11,298,337 B2
(45) Date of Patent: Apr. 12, 2022

(54) PARTHENOLIDE AND ITS DERIVATIVE FOR USE IN THE TREATMENT OF AXONAL DAMAGE

(71) Applicant: RUHR-UNIVERSITÄT BOCHUM, Bochum (DE)

(72) Inventors: Philipp Ludwig Alexander Gobrecht, Bad Hersfeld (DE); Dietmar Fischer, Dormagen (DE)

(73) Assignee: RUHR-UNIVERSITÄT BOCHUM, Bochum (DE)

( * ) Notice: Subject to any disclaimer, the term of this patent is extended or adjusted under 35 U.S.C. 154(b) by 0 days.

(21) Appl. No.: 16/555,461

(22) Filed: Aug. 29, 2019

(65) Prior Publication Data

US 2019/0388388 A1 Dec. 26, 2019

Related U.S. Application Data

(63) Continuation of application No. 15/567,823, filed as application No. PCT/EP2016/055118 on Mar. 10, 2016, now abandoned.

(30) Foreign Application Priority Data

Apr. 20, 2015 (EP) .................................. 15164307

(51) Int. Cl.
 *A61K 31/365* (2006.01)
 *A61K 45/06* (2006.01)

(52) U.S. Cl.
 CPC ............ *A61K 31/365* (2013.01); *A61K 45/06* (2013.01)

(58) Field of Classification Search
 CPC .............................. A61K 31/365; A61K 45/06
 See application file for complete search history.

(56) References Cited

FOREIGN PATENT DOCUMENTS

| CN | 102 579 426 A | 7/2012 |
| EP | 1 700 596 A1 | 9/2006 |
| WO | 2006/094811 A2 | 9/2006 |

OTHER PUBLICATIONS

Fawcett JW. "Spinal Cord Repair: From Experimental Models to Human Applicaiton." Spinal Cord. Dec. 1998, 36(12): 811-817. [Abstract Only].*
Nacimiento et al. "Nerve regeneration after spinal cord trauma. Neurobiological progress and clinical expectations." Nervenarzt. Aug. 1999. 70(8): 702-713. [Abstract only].*
Dietz et al. "Neurological Aspects of Spinal-Cord Repair: Promises and Challenges." Lancet Neurol., 2006; 5:688-694.*
European Office Action dated Feb. 28, 2020 from corresponding European Application No. 16 709 069.5.
Gerdts et al. "Image-based Screening Identifies Novel Roles for I[kappa]B Kinase and Glycogen Synthase Kinase 3 in Axonal Degeneration" Journal of Biological Chemistry, vol. 286, No. 32, pp. 28011-28018 (Aug. 12, 2011).
Altmann et al. "Anticancer drugs from nature?natural products as a unique source of new microtubule-stabilizing agents" Natural Product Reports, vol. 24, No. 2, p. 327 (Jan. 1, 2007).
Baas et al. "Beyond taxol: microtubule-based treatment of disease and injury of the nervous system" Brain, vol. 136, No. 10, pp. 2937-2951 (Jun. 27, 2013).
Fonrose et al. "Parthenolide Inhibits Tubulin Carboxypeptidase Activity" Cancer Research, vol. 67, No. 7, pp. 3371-3378 (Apr. 1, 2007).
International Search Report published in International Patent Application No. PCT/EP2016/055118 dated Apr. 19, 2016.
Popiolek-Barczyk et al. Inhibition of intracellular signaling pathways NF-kappaB and MEK1/2 attenuates neuropathic pain development and enhances morphine analgesia. Pharmacological Reports, 66, pp. 845-851, (May 19, 2014).
Ghantous et al. Parthenolide: from plant shoots to cancer roots. Drug Discovery Today, vol. 18, Nos. 17/18. (Sep. 2013).
Karin Jöhrer et al. "Antimyeloma activity of the sesquiterpene lactone cnicin: impact on Pim-2 kinase as a novel therapeutic target" J Mol Med (2012); Published on Dec. 29, 2011; pp. 681-693.

* cited by examiner

*Primary Examiner* — Jared Barsky
(74) *Attorney, Agent, or Firm* — Davidson, Davidson & Kappel, LLC

(57) ABSTRACT

The present invention relates to a compound reducing microtubule detyrosination in axonal tips selected from the group consisting of tubulin carboxypeptidase inhibitors and tubulin tyrosine ligase activators and combinations thereof for use in the treatment of axonal damage.

2 Claims, 6 Drawing Sheets

PARTHENOLIDE AND ITS DERIVATIVE FOR USE IN THE TREATMENT OF AXONAL DAMAGE

Figure 1:
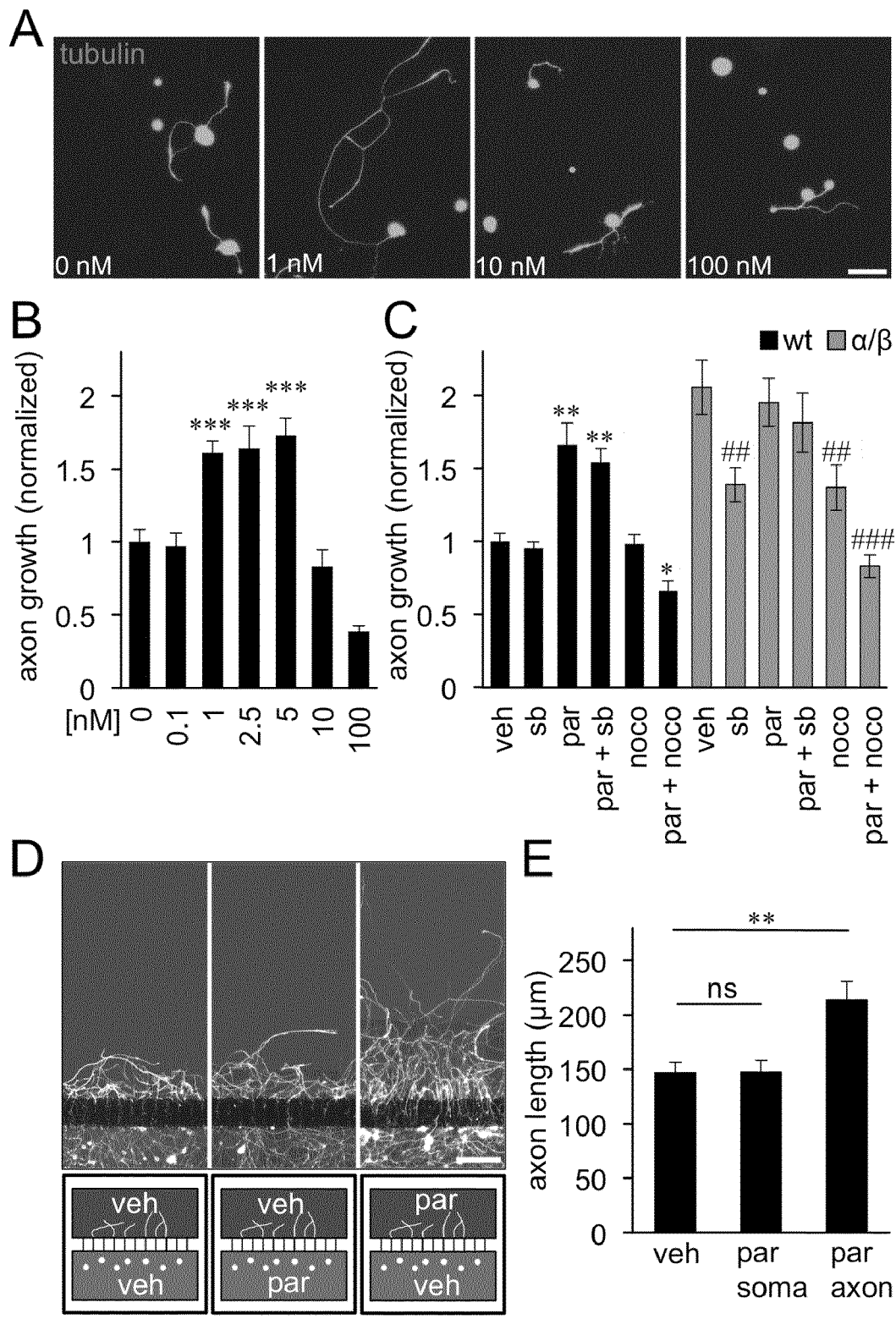

This application is a continuation of U.S. application Ser. No. 15/567,832 filed on Oct. 19, 2017, which is a U.S. national phase application under 35 U.S.C. of § 371 of International Application No. PCT/EP2016/055118, filed Mar. 10, 2016, the disclosures of which are hereby incorporated by reference herein.

The present invention relates to the treatment of axonal damage upon nerve injury or disease.

The complex, delicate structures of the nervous system, the brain, spinal cord and peripheral nerves, are susceptible to various types of damage. Injury to peripheral nerves (peripheral neuropathy) for example can occur through a variety of trauma, including laceration, focal contusion (gunshot wounds), stretch/traction injury, compression, drug injection injury or electrical injury. Moreover, peripheral neuropathy can be the result of systemic diseases such as diabetes or leprosy, vitamin deficiency, medication e.g., chemotherapy, radiation therapy, excessive alcohol consumption, immune system disease or viral infection. Axonal damage in the CNS may be caused by cut, rupture or compression/contusion or be be associated with diseases inflicting injury on the axon, for example axonal damage and axonal break caused by stroke or multiple sclerosis.

Peripheral nerve damage is a common cause of considerable functional morbidity, and healthcare expenditure. Surgery can be done in case of a peripheral nerve cut or rupture. In peripheral nerve reconstruction the injured nerve is identified and exposed so that normal nerve tissue can be examined above and below the level of injury, injured portions of the nerve are removed and the cut nerve endings are then carefully reapproximated. A large section of injuries however is unsuitable for primary repair, and standard clinical management results in inadequate sensory and motor restoration in the majority of cases, despite the rigorous application of complex microsurgical techniques.

In general, injured peripheral nervous tissue possesses the capacity to regenerate severed axons and therefore the ability for repair. Mechanisms of so-called neuroregeneration may include generation of new glia, extension of axons, re-myelination or restoration of functional synapses. However, the ability for neuroregeneration differs strongly between the peripheral nervous system (PNS) and the central nervous system (CNS). In contrast to the peripheral nervous system, central nervous axon regeneration is very limited due to an inhibitory axonal environment caused by myelin derived factors and the formation of an inhibitory glial scar. Moreover, CNS neurons have a much lower intrinsic ability to regrow injured axon. However, although injured axons of the PNS show generally greater potential for intrinsic axonal regrowth, functional regeneration is often limited, mainly due to a decline in neurotrophic support from Schwann cells over time and axonal misguidance. These aspects become particularly evident in cases of long distance regeneration, for example after sciatic nerve injury in legs or median nerve damage in arms. Therefore, the development of novel therapeutic measures aiming to accelerate axon regeneration and thereby improving functional recovery is highly desirable.

Therefore, the object underlying the present invention was to provide compounds being usable in the treatment of axonal damage.

The problem is solved by a compound reducing microtubule detyrosination in axonal tips selected from the group consisting of tubulin carboxypeptidase (TCP) inhibitors and tubulin tyrosine ligase (TTL) activators and combinations thereof for use in the treatment of axonal damage.

Surprisingly, it was found that the TCP inhibitor parthenolide markedly promoted axon growth of adult dorsal root ganglion neurons in culture. Moreover, application of the drug in vivo accelerated axon growth and promoted functional sciatic nerve regeneration in wild-type mice compared to respective controls. This could be shown for local and systemic drug application. Therefore, TCP inhibitors such as parthenolide and TTL activators provide a promising pharmacological treatment for nerve injuries and improvement of nerve repair.

It is assumed that the advantageous effects of parthenolide are derived due to a reduction of tubulin detyrosination in axonal tips by pharmacological inhibition of a protein denoted tubulin carboxypeptidase (TCP). As used herein, the term "tubulin carboxypeptidase inhibitor" refers to a class of drugs that target and inhibit the activity of TCP, which cleaves off the -Glu-Tyr bond to release the C-terminal tyrosine residue from the native tyrosinated tubulin or inhibit microtubule detyrosination. As used herein, the term "tubulin tyrosine ligase activator" refers to drugs that target and activate the activity of a protein denoted tubulin tyrosine ligase (TTL), which on the other hand adds the COOH-terminal tyrosine residue to tubulin. The TCP inhibitor parthenolide increased axon regeneration in cell culture. Strikingly, intraneural or intraperitoneal application of the TCP inhibitor in vivo markedly promoted sciatic nerve regeneration and accelerated functional recovery the injured animal. Thus, pharmacological approaches reducing microtubule detyrosination in axonal tips provide a novel, clinically suitable strategy to significantly improve nerve repair and repair of central projectories and treat axonal damage. Advantageously, local and systemic application of a drug was shown to be effective.

As used herein, the term "axon" refers to a long, slender projection of a peripheral or central neuron. The axon typically conducts electrical impulses away from the neuron's cell body. The axon and its insulating sheath is called nerve fiber. In the central nervous system, myelin is produced by oligodendrocytes. In the peripheral nervous system, myelin is formed by Schwann cells. A peripheral nerve fiber comprises an axon, myelin sheath, Schwann cells and its endoneurium, a central nerve fiber will not comprise Schwann cells and endoneurium, but instead oligodendrocytes. As used herein, the term "axonal tip" refers to the terminal end or ends of an axon. At the tip of the axon is a dynamic compartment called growth cone, via which growing axons move through their environment.

As used herein, the term "axonal damage" refers to damage to axons of any nerve fibers and nervous tissue. The term "nerve" as used herein refers to sensory fibers, motor fibers, or both. The term "axonal damage" refers to nerve injuries and to peripheral neuropathies caused by axonal damage, and also to damage of the optic nerve or spinal cord. Peripheral neuropathy can be the result of systemic diseases such as diabetes or leprosy, vitamin deficiency, medication e.g., chemotherapy, radiation therapy, excessive alcohol consumption, immune system disease or viral infection. Axonal damage may manifest upon nerve injury or disease. Nerve injury may be inflicted on nerves of the peripheral nervous system for example by a break or cutting of limbs, and also the spinal cord may be injured by cut, rupture or compression/contusion. Axonal damage also may be associated with diseases inflicting injury on the axon, for example axonal damage and axonal break caused by stroke or multiple sclerosis.

Nerve injury may be caused through a trauma such as laceration, focal contusion, stretch/traction injury, compression, drug injection injury or electrical injury. Particular damage is a nerve cut, rupture or compression/contusion. Nerve injuries according to Seddon are classified correlating the degree of injury with symptoms, pathology and prognosis based on three main types of nerve fiber injury and whether there is continuity. Neurapraxia refers to a disorder of the peripheral nervous system in which the axon remains intact, but there is myelin damage causing an interruption in conduction of the impulse down the nerve fiber. Axonotmesis refers to a type of injury being the result of a more severe crush or contusion than neuropraxia wherein both the nerve fibers and the nerve sheath are disrupted. Neurotmesis is the most severe lesion, which occurs on severe contusion, stretch or laceration. Not only the axon, but the encapsulating connective tissue lose their continuity. The extreme degree of neurotmesis is transsection. In embodiments, nerve injury refers to axonotmesis or neurotmesis.

In embodiments the axonal damage hence is an injury of the peripheral nervous system or the central nervous system that causes functional loss of the neuron. In preferred embodiments, the axonal damage is an injury of the sciatic nerve or the optic nerve or central projections of the spinal cord. Axonal damage of the optic nerve or central projections of the spinal cord is a preferred injury of the central nervous system. A further preferred axonal damage of peripheral nerves as is the sciatic nerve, is a damage of nerves projecting into arms and fingers. The sciatic nerve or nerves projecting into arms and fingers are long nerves and particularly vulnerable to damage. Damage can lead to irreversible loss of sensory and motor function as well as pain to patients. Injury of the optic nerve often leads to lifelong and severe impairment of eyesight or even complete blindness of the respective eye. Moreover, axon regeneration does normally not occur in the injured spinal cord, which comprises other central projectories of axons. Axonal damage can lead to severe disabilities such as tetra- or paraplegia. For this reason the axon growth promoting effect of parthenolide may advantageously improve the clinical outcome after spinal cord injuries. In other embodiments, the axonal damage is an injury of a cranial nerve, particularly the optic nerve or trigeminal nerve, particular its ophthalmic branch. In further embodiments, the axonal damage is an injury of plexus brachialis or the nerves that innervate internal organs.

Further impairments or diseases caused by axonal damage may be selected from the group comprising glaucoma, in cases where axons are damaged in the optic nerve head. In embodiments, the axonal damage is associated with peripheral neuropathy, glaucoma, stroke or multiple sclerosis. Examples for peripheral neuropathies are diabetic neuropathy and cytostatics-induced neuropathy.

In further embodiments, the axonal damage is associated with an injury of the cornea or a denervation of a transplanted cornea, or axotomized fibres in the lesioned optic nerve or trigeminal nerve, particular its ophthalmic branch. An injury of the cornea may be caused by a cutting or abrasion. The cornea generally is the most densely innervated tissue on the surface of the body. A corneal transplantation however results in a cutting of corneal axons and thus in complete denervation of the transplanted cornea. Re-innervation to the donor tissue is highly variable, and in many cases hypoesthesia persists for many years after initial surgery. A promotion of growth from axons arising from N. ophthalmicus into the cornea particularly a transplanted cornea thus is highly advantageous.

As parthenolide has shown to directly interact with axonal growth cones it is likely that axon growth in the cornea is accelerated by parthenolide. Advantageously, it could be demonstrated that parthenolide not only was able to promote nerve regeneration of peripheral nerves but also of central neurons such as retinal ganglion cells, which indicates that parthenolide might be useful in the treatment of glaucoma or axotomized fibers in the lesioned optic nerve.

Preferred compounds reducing microtubule detyrosination in axonal tips for use in the treatment of axonal damage are tubulin carboxypeptidase inhibitors. A preferred tubulin carboxypeptidase inhibitor is parthenolide or a racemate, enantiomer, stereoisomer, solvate, hydrate, pharmaceutically acceptable salt, ester and/or derivative or structural analogue thereof. Parthenolide is a sesquiterpene lactone, which typically is extracted from *Tanacetum parthenium*, a plant also known as feverfew, a member of the Asteraceae family Parthenolide is the name of a 4,5-epoxy-6α-hydroxy-gamma-lactone. The chemical formula (1) of parthenolide is given below:

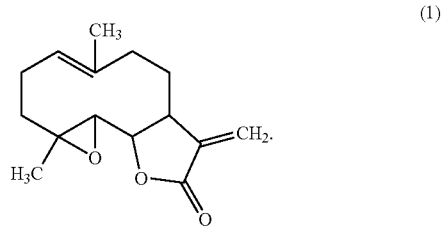 [SMILES: C=C1C(=O)OC2C1CC/C(C)=C/CCC1(C)OC21]

(1)

Parthenolide comprises chiral centres and thus its racemates, enantiomers or stereoisomers are possible and also usable. A preferred stereoisomer of parthenolide is given in formula (1a) below:

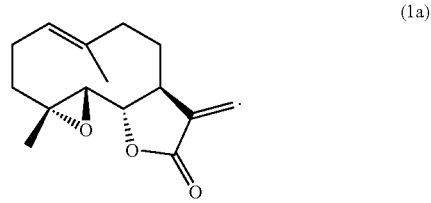 [SMILES: C=C1C(=O)O[C@H]2[C@H]1CC/C(C)=C/CC[C@@]1(C)O[C@@H]21]

(1a)

Parthenolide also is denoted (1aR, 4E, 7aS, 10aS, 10bR)-1a,5-Dimethyl-8-methylene-2, 3, 6, 7, 7a, 8, 10a, 10b-octahydrooxireno[9,10]cyclodeca[1,2-b]furan-9(1aH)-one according to the IUPAC nomenclature. It could be shown that parthenolide can markedly promote axon growth of neurons in vitro and promote peripheral nerve regeneration (sciatic nerve) and markedly accelerate functional recovery in vivo after injury. Moreover, it promotes neurite growth of CNS neurons, such as cultured retinal ganglion cells.

In embodiments also derivatives or structural analogues of parthenolide are usable for TCP inhibition. In embodiments the parthenolide derivative is selected from the group comprising 8-, 9- or 14-hydroxy parthenolide and/or 13-amino parthenolides such as 13-dimethylamino parthenolide usually referred to as dimethylamino parthenolide (DMAPT). Dimethylamino parthenolide (DMAPT) advantageously is a water-soluble and orally bioavailable parthenolide derivative.

Such parthenolide derivatives can increase the solubility of the compound, which may be advantageous for formulating suitable pharmaceutical formulations and provides for improved biological availability of the compound in aqueous environments. Hydroxy derivatives may be selected from the group comprising 8-, 9- or 14-hydroxy parthenolide, particularly hydroxy-8a-parthenolide. 13-amino parthenolide derivatives may be selected from the group comprising 11βH, 13-Dimethylaminoparthenolide, 11βH, 13-Diethylaminoparthenolide 11βH, 13-(tert-Butylamino) parthenolide, 11βH, 13-(Pyrrolidin-1-yl) parthenolide, 11βH, 3-(Piperidin-1-yl) parthenolide, 11βH, 13-(Morpholin-1-yl)parthenolide, 11βH, 13-(4-Methylpiperidin-1-yl) parthenolide, 11βH, 13-(4-Methylpiperazin-1-yl) parthenolide, 11βH, 13-(Homopiperidin-1-yl) parthenolide, 11βH, 13-(Heptamethyleneimin-1-yl) parthenolide, 11βH, 13-(Azetidin-1-yl) parthenolide and/or 11βH, 13-Diallylaminoparthenolide. A preferred aminoparthenolide is 13-dimethylamino parthenolide.

Structural analogues of parthenolide can also function as TCP inhibitors. In embodiments the parthenolide structural analogue is selected from the group comprising cnicin, the compounds according to formulas (2) and (3) as indicated below and/or racemates, enantiomers, stereoisomers, solvates, hydrates, and pharmaceutically acceptable salts and/or esters thereof:

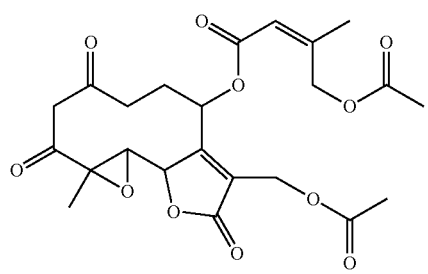

(2)

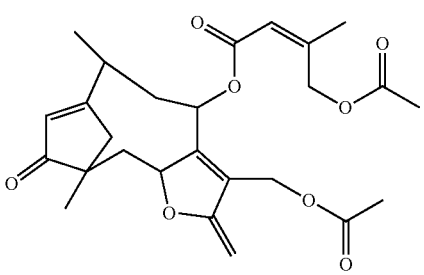

(3)

Cnicin also is denoted [(1R,2S,4E,8Z,10S)-8-(hydroxymethyl)-4-methyl-13-methylidene-12-oxo-11-oxabicyclo[8.3.0]trideca-4,8-dien-2-yl] (3S)-3,4-dihydroxy-2-methylidene-butanoate or [(3aR,4S,6E,10Z,11aR)-10-(hydroxymethyl)-6-methyl-3-methylidene-2-oxo-3a,4,5,8,9,11a-hexahydrocyclodeca[b]furan-4-yl] (3R)-3,4-dihydroxy-2-methylidene-butanoate according to the IUPAC nomenclature. A preferred stereoisomer of cnicin is given in formula (4) below:

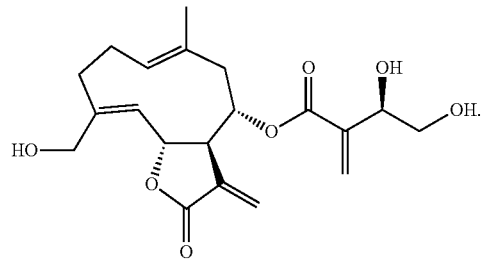

(4)

Parthenolide further can be available in the form of its solvates, hydrates, and pharmaceutically acceptable salts and esters. The term "pharmaceutically acceptable salt" refers to salts prepared from pharmaceutically acceptable non-toxic bases or acids. A pharmaceutically acceptable salt can be conveniently prepared from pharmaceutically acceptable non-toxic bases, including inorganic bases and organic bases, organic anions, organic cations, halides or alkaline. The term pharmaceutically acceptable salt includes alkali metal salts and addition salts of free acids or free bases. Suitable pharmaceutically acceptable base addition salts of the fusion proteins include metallic salts and organic salts. Preferred salts derived from inorganic bases include ammonium, calcium, magnesium, potassium and sodium salts. Salts derived from pharmaceutically acceptable organic non-toxic bases include salts of primary, secondary, and tertiary amines Parthenolide and its derivatives or analogues may be used in the form of a hydrochloride or maleate.

Particularly for intraneural application concentrations of the compound, particularly parthenolide, may be in the range from ≥0.01 μM to ≤10 μM, particularly in the range from ≥0.01 μM to ≤1 μM, or from ≥0.05 μM to ≤0.1 μM, or from ≥0.05 μM to ≤1 μM.

The compound reducing microtubule detyrosination such as parthenolide can be used in the treatment of axonal damage alone or in combination with other therapeutic ingredients. In embodiments, the compound reducing microtubule detyrosination as given above such as parthenolide can be used in combination with a compound selected from paclitaxel, epothilone B and/or a ROCK inhibitor such as Y27632. Paclitaxel is denoted (2α, 4α, 5β, 7β, 10β, 13α)-4,10-Bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate according to IUPAC nomenclature and is available under the trade name Taxol. A combination with paclitaxel or epothilone B may be particularly advantageous for a treatment of axonal damage of the central nervous system. As used herein, the term "ROCK inhibitor" refers to drugs that target and inhibit the activity of a protein denoted Rho-associated protein kinase (ROCK). A suitable ROCK inhibitor is a compound denoted Y27632 or (1R,4r)-4-((R)-1-aminoethyl)-N-(pyridin-4-yl)cyclohexanecarboxamide dihydrochloride.

The compound reducing microtubule detyrosination in axonal tips can be formulated as a pharmaceutical composition. A further aspect of the present invention relates to a pharmaceutical composition comprising as an active ingredient a compound reducing microtubule detyrosination in axonal tips selected from the group consisting of tubulin carboxypeptidase inhibitors and tubulin tyrosine ligase activators and combinations thereof for use in the treatment of axonal damage.

A preferred compound is a TCP inhibitor. In embodiments of the pharmaceutical composition, the TCP inhibitor is parthenolide or a racemate, enantiomer, stereoisomer, solvate, hydrate, pharmaceutically acceptable salt, ester and/or derivative or structural analogue thereof. In embodiments the parthenolide derivative is selected from the group comprising 8-, 9- or 14-hydroxy parthenolide and/or 13-amino parthenolides such as 13-dimethylamino parthenolide (DMAPT). Hydroxy-derivatives may be selected from the group comprising 8-, 9- or 14-hydroxy parthenolide, particularly hydroxy-8a-parthenolide. 13-amino parthenolide derivatives may be selected from the group comprising 11βH, 13-Dimethylaminoparthenolide, 11βH, 13-Diethylaminoparthenolide 11βH, 13-(tert-Butylamino) parthenolide, 11βH, 13-(Pyrrolidin-1-yl) parthenolide, 11βH, 3-(Piperidin-1-yl) parthenolide, 11βH, 13-(Morpholin-1-yl) parthenolide, 11βH, 13-(4-Methylpiperidin-1-yl) parthenolide, 11βH, 13-(4-Methylpiperazin-1-yl) parthenolide, 11βH, 13-(Homopiperidin-1-yl) parthenolide, 11βH, 13-(Heptamethyleneimin-1-yl) parthenolide, 11βH, 13-(Azetidin-1-yl) parthenolide and/or 11βH, 13-Diallylaminoparthenolide. A preferred aminoparthenolide is 13-dimethylamino parthenolide. In further embodiments the parthenolide structural analogue is selected from the group comprising cnicin, the compounds according to formulas (2) and (3) and/or racemates, enantiomers, stereoisomers, solvates, hydrates, and pharmaceutically acceptable salts and/or esters thereof.

In embodiments, the pharmaceutical composition is for use in the treatment of axonal damage of the peripheral nervous system or the central nervous system, particularly an injury of the sciatic nerve or the optic nerve or central projections of the spinal cord. In embodiments, the pharmaceutical composition is for use in the treatment of axonal damage associated with peripheral neuropathy, glaucoma, stroke or multiple sclerosis. Examples for peripheral neuropathies are diabetic neuropathy and cytostatic-induced neuropathy. In further embodiments, the pharmaceutical composition is for use in the treatment of axonal damage which is associated with a denervation of an injured or transplanted cornea, or is associated with axotomized fibers in the lesioned optic nerve or trigeminal nerve, particular its ophthalmic branch.

The pharmaceutical composition can comprise a compound reducing microtubule detyrosination in axonal tips according to the invention as an active ingredient, a pharmaceutically acceptable carrier and optionally other therapeutic ingredients or adjuvants. The present invention hence also relates to a pharmaceutical composition for use in the treatment of axonal damage wherein the composition comprises as an active ingredient a compound reducing microtubule detyrosination in axonal tips according to the invention and a pharmaceutically acceptable carrier.

The compound can be dissolved or dispersed in a pharmaceutically acceptable carrier. The term "pharmaceutical or pharmacologically acceptable" refers to molecular entities and compositions that do not produce an adverse, allergic or other untoward reaction when administered to a subject, such as, for example, a human, as appropriate. The pharmaceutical carrier can be, for example, a solid, liquid, or gas. Suitable carriers and adjuvants can be solid or liquid and correspond to the substances ordinarily employed in formulation technology for pharmaceutical formulations. For example, water, glycols, oils, alcohols and the like may be used to form liquid preparations such as solutions. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

The composition can be suitable for oral or parenteral administration. Parenteral administration includes subcutaneous, intramuscular, intravenous, intraneural, periradicular, intraperitoneal and local administration. In embodiments the composition is formulated for local such as intraneural or periradicular application, or for systemic application such as intraperitoneal, intravenous, subcutaneous or oral application. For treatment of peripheral nerves the composition may be administered systemically or intraneurally for example into the sciatic nerve. Also local or topical application such as periradicular application may be preferred. In further embodiments, the composition is formulated for intraocular application or as eye drops. Administration in the form of eye drops particularly may be useful in the treatment of an injured or transplanted cornea or glaucoma, or axotomized fibers in the lesioned optic nerve or trigeminal nerve, particular its ophthalmic branch. Compositions suitable for injectable use include sterile aqueous solutions or dispersions.

Particularly for intraneural application concentrations of the compound, particularly parthenolide, may be in the range from ≥0.01 μM to ≤10 μM, particularly in the range from ≥0.01 μM to ≤1 μM, or from ≥0.05 μM to ≤0.1 μM, or from ≥0.05 μM to ≤1 μM. It was found that already concentrations ranging from 0.01 μM to 0.1 μM markedly and similarly increased axon regeneration after sciatic nerve injury in vivo, while higher concentrations >10 μM rather reduced it.

For example for a treatment of the central nervous system it may be also administered locally, for example by nerve injection, mini-pumps etc., but it is preferred to administer the composition via an alimentary route. Specifically, the pharmaceutical composition may be administered systemically, for example orally, systemically or intraperitoneally. In further embodiments, the composition may be administered as eye drops. Intraocular administration in the form of eye drops particularly may be useful in the treatment of an injured cornea, or a transplanted cornea, or glaucoma, or axotomized fibers in the lesioned optic nerve or trigeminal nerve, particular its ophthalmic branch. The pharmaceutical compositions may be conveniently presented in unit dosage form and prepared by any of the methods well known in the art of pharmacy. The pharmaceutical composition may be produced under sterile conditions using standard pharmaceutical techniques well known to those skilled in the art.

The pharmaceutical composition can comprise a compound reducing microtubule detyrosination such as parthenolide alone or in combination with other therapeutic ingredients. Preferred therapeutic ingredients provide a disinhibitory effects towards central myelin or inhibitory factors of the glial scar. In embodiments, the pharmaceutical composition comprises as an active ingredient a combination of a compound reducing microtubule detyrosination such as parthenolide as given above, and a compound selected from paclitaxel, epothilone B and/or a ROCK inhibitor such as Y27632. A pharmaceutical composition comprising paclitaxel or epothilone B as a further therapeutic ingredient may be particularly advantageous for a treatment of axonal damage in the central nervous system.

The present invention also relates to the use of a compound reducing microtubule detyrosination in axonal tips selected from the group consisting of tubulin carboxypeptidase inhibitors and tubulin tyrosine ligase activators and combinations thereof for the manufacture of a medicament for the treatment of axonal damage. In embodiments the TCP inhibitor is parthenolide or a racemate, enantiomer, stereoisomer, solvate, hydrate, pharmaceutically acceptable salt, ester and/or derivative or structural analogue thereof. In embodiments the parthenolide derivative is selected from the group comprising 8-, 9- or 14-hydroxy parthenolide and/or 13-amino parthenolide such as 13-dimethylamino parthenolide (DMAPT). Hydroxy derivatives may be selected from the group comprising 8-, 9- or 14-hydroxy parthenolide, particularly hydroxy-8a-parthenolide. 13-amino parthenolide derivatives may be selected from the group comprising 11βH, 13-Dimethylaminoparthenolide, 11βH, 13-Diethylaminoparthenolide 11βH, 13-(tert-Butylamino) parthenolide, 11βH, 13-(Pyrrolidin-1-yl) parthenolide, 11βH, 3-(Piperidin-1-yl) parthenolide, 11βH, 13-(Morpholin-1-yl)parthenolide, 11βH, 13-(4-Methylpiperidin-1-yl) parthenolide, 11βH, 13-(4-Methylpiperazin-1-yl) parthenolide, 11βH, 13-(Homopiperidin-1-yl) parthenolide, 11βH, 13-(Heptamethyleneimin-1-yl) parthenolide, 11βH, 13-(Azetidin-1-yl) parthenolide and/or 11βH, 13-Diallylaminoparthenolide. A preferred aminoparthenolide is 13-dimethylamino parthenolide. In further embodiments the parthenolide structural analogue is selected from the group comprising cnicin, the compounds according to formulas (2) and (3) and/or racemates, enantiomers, stereoisomers, solvates, hydrates, and pharmaceutically acceptable salts and/or esters thereof. In embodiments the axonal damage is an injury of the peripheral nervous system or the central nervous system, particularly an injury of the sciatic nerve or the optic nerve or central projections of the spinal cord. In embodiments, the axonal damage is associated with peripheral neuropathy, glaucoma, stroke or multiple sclerosis. Examples for peripheral neuropathies are diabetic neuropathy and cytostatics-induced neuropathy. In further embodiments, the axonal damage is associated with a denervation of an injured or transplanted cornea, or is associated with axotomized fibers in the lesioned optic nerve or trigeminal nerve, particular its ophthalmic branch.

The compound reducing microtubule detyrosination such as parthenolide can be used alone or in combination with other therapeutic substances. In embodiments, the use relates to the use of a compound reducing microtubule detyrosination such as parthenolide as given above and a compound selected from paclitaxel, epothilone B and/or a ROCK inhibitor such as Y27632 for the manufacture of a medicament for the treatment of axonal damage.

A further aspect of the present invention relates to a method of treating axonal damage, the method comprising administering to a subject a therapeutically effective amount of a compound reducing microtubule detyrosination in axonal tips selected from the group consisting of tubulin carboxypeptidase inhibitors and tubulin tyrosine ligase activators and combinations thereof.

Subjects include both human subjects and animal subjects, particularly mammalian subjects such as human subjects or mice or rats for medical purposes. The term "therapeutically effective amount" is used herein to mean an amount or dose sufficient to cause an improvement in a clinically significant condition in the subject.

In embodiments the method refers to administering a TCP inhibitor. In embodiments the TCP inhibitor is parthenolide or a racemate, enantiomer, stereoisomer, solvate, hydrate, pharmaceutically acceptable salt, ester and/or derivative or structural analogue thereof. In embodiments the parthenolide derivative is selected from the group comprising 8-, 9- or 14-hydroxy parthenolide and/or 13-amino parthenolide such as 13-dimethylamino parthenolide (DMAPT). Hydroxy derivatives may be selected from the group comprising 8-, 9- or 14-hydroxy parthenolide, particularly hydroxy-8a-parthenolide. 13-amino parthenolide derivatives may be selected from the group comprising 11βH, 13-Dimethylaminoparthenolide, 11βH, 13-Diethylaminoparthenolide 11βH, 13-(tert-Butylamino) parthenolide, 11βH, 13-(Pyrrolidin-1-yl) parthenolide, 11βH, 3-(Piperidin-1-yl) parthenolide, 11βH, 13-(Morpholin-1-yl)parthenolide, 11βH, 13-(4-Methylpiperidin-1-yl) parthenolide, 11βH, 13-(4-Methylpiperazin-1-yl) parthenolide, 11βH, 13-(Homopiperidin-1-yl) parthenolide, 11βH, 13-(Heptamethyleneimin-1-yl) parthenolide, 11βH, 13-(Azetidin-1-yl) parthenolide and/or 11βH, 13-Diallylaminoparthenolide. Structural analogues of parthenolide can also function as TCP inhibitors. A preferred aminoparthenolide is 13-dimethylamino parthenolide. In further embodiments the parthenolide structural analogue is selected from the group comprising cnicin, the compounds according to formulas (2) and (3) and/or racemates, enantiomers, stereoisomers, solvates, hydrates, and pharmaceutically acceptable salts and/or esters thereof.

In embodiments, the method relates to administering a compound reducing microtubule detyrosination such as parthenolide as given above and a compound selected from paclitaxel, epothilone B and/or a ROCK inhibitor such as Y27632.

In embodiments the axonal damage is an injury of the peripheral nervous system or the central nervous system, particularly an injury of the sciatic nerve or the optic nerve or central projections of the spinal cord. In embodiments, the axonal damage is associated with peripheral neuropathy, glaucoma, stroke or multiple sclerosis. Examples for peripheral neuropathies are diabetic neuropathy and cytostatic-induced neuropathy. In further embodiments, the axonal damage is associated with a denervation of an injured or transplanted cornea, or is associated with axotomized fibers in the lesioned optic nerve or trigeminal nerve, particular its ophthalmic branch.

The treatment may include oral or parenteral administration. Parenteral administration includes subcutaneous, intramuscular, intravenous, intraneural, periradicular, intraperitoneal and intraperitoneal administration. In embodiments the composition is administered via intraneural, periradicular, intraperitoneal, intravenous, subcutaneous or oral route. For treatment of peripheral nerves the composition may be administered intraneurally for example into the sciatic nerve. Also local parthenolide application such as periradicular application may be preferred. Particularly for intraneural application concentrations of the compound, particularly parthenolide, may be in the range from ≥0.01 μM to ≤10 μM, particularly in the range from ≥0.01 μM to ≤1 μM, or from ≥0.05 μM to ≤0.1 μM, or from ≥0.05 μM to ≤1 μM. For treatment of the central nervous system for example it may be preferred to administer the composition via an alimentary route. For the treatment of injured corneal tissue or a transplanted cornea or glaucoma it may be preferred to administer the composition as eye drops.

The treatment may be a continuous prolonged treatment, or include a single or few time administrations. It was found that already one single injection was sufficient to significantly accelerate functional regeneration of the sciatic nerve in vivo compared to vehicle treated control.

Unless otherwise defined, the technical and scientific terms used herein have the same meaning as commonly understood by one of ordinary skill in the art to which this invention belongs.

The examples which follow serve to illustrate the invention in more detail but do not constitute a limitation thereof.

The figures show:

FIG. 1 FIG. 1A shows dissociated DRG neurons of wt mice treated with various parthenolide concentrations as indicated and stained with βIII-tubulin after 2 days in culture. Scale bar: 100 μm. FIG. 1B shows the quantification of axon growth of the neuronal cultures. The error bars represent the standard error of the mean. Statistical significance was determined with ANOVA and the post hoc Holm Sidac test. Treatment effects compared to vehicle treated control group: *p≤0.001. FIG. 1C shows quantification of axon growth of dissociated dorsal root ganglion (DRG) neurons from wt or GSK3$^{S/A}$ double knockin mice (α/β), treated with either vehicle (−), 5 μM GSK3 inhibitor SB216763 (sb), 1 nM parthenolide (par), a combination of 5 μM sb and 1 nM par, 10 nM nocodazole (noco) or a combination of par+noco after 2 days in culture. The error bars represent the standard error of the mean. Statistical significance was determined with ANOVA and the post hoc Holm Sidac test. Treatment effects compared to vehicle treated wt-group: *p≤0.001; p≤0.01. Treatment effects compared to vehicle treated α/β-group $^{###}$p≤0.001; $^{##}$p≤0.01. FIG. 1D shows cultures showing βIII-tubulin-positive axons of adult DRG neurons growing through microchannels of two-compartment chambers 1 day after axotomy. Vehicle (veh) or 5 nM parthenolide were either applied into the somal (par, soma) or in the axonal compartments (par, axon) as indicated. Scale bar: 250 μM. FIG. 1E shows the quantification of axon growth of cultures through microchannels of two-compartment chambers 1 day after axotomy. Data from 5 experiments were averaged. The error bars represent the standard error of the mean. Statistical significance was determined with ANOVA and the post hoc Holm Sidac test. Treatment effects: p≤0.01.

Figure 2:
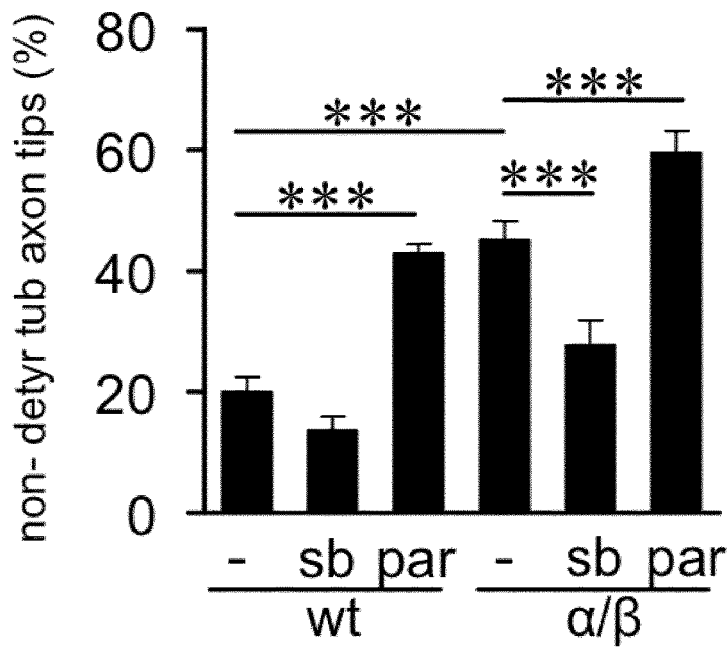

FIG. 2 shows the quantification of non-detyrosinated tubulin-positive axon tips of cultures from wild type (wt) and GSK3S/A double knockin mice (α/β) 3 days after exposure to vehicle (−), 5 μM SB216763 (sb) or 10 nM parthenolide (par). Data from three independent experiments were normalized to the vehicle treated wt group. The error bars represent the standard error of the mean. Statistical significance was determined with ANOVA and the post hoc Holm Sidac test. Treatment effects: ***p≤0.001.

Figure 3:
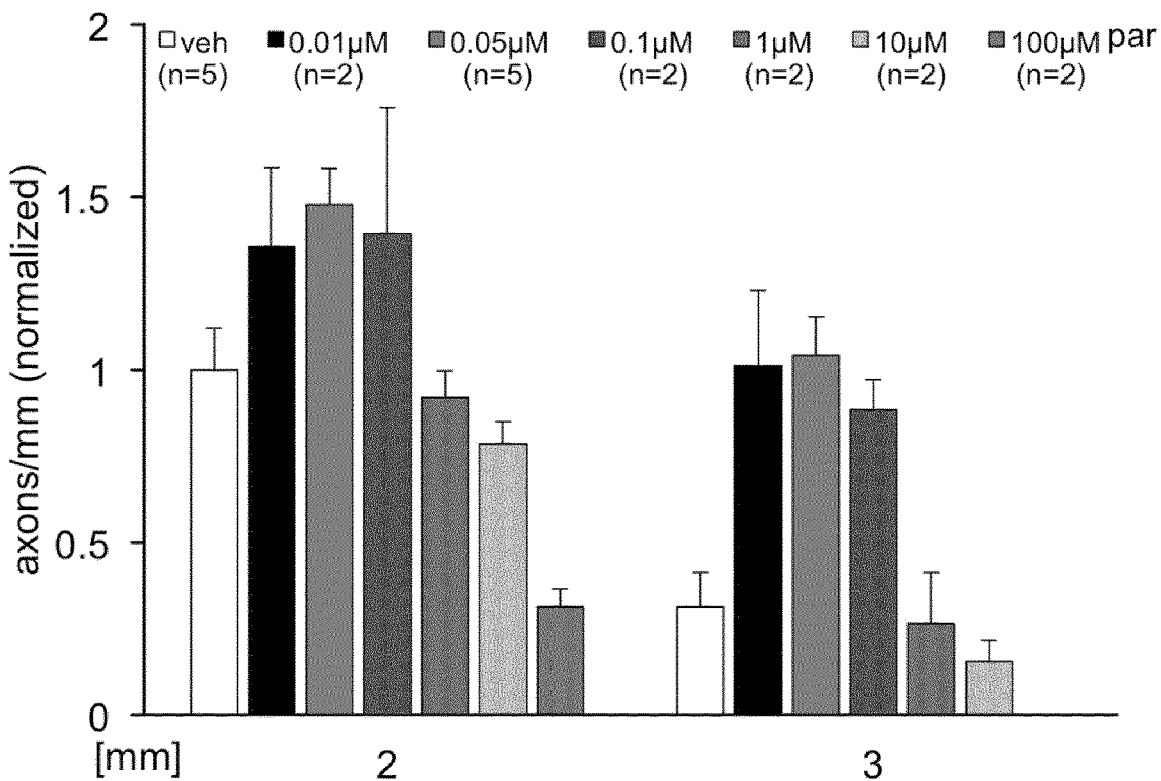

FIG. 3 Quantification of axon regeneration into the sciatic nerve 3 days after sciatic nerve crush based on SCG10 stained axons after treatment with vehicle (veh) or various parthenolide concentrations as indicated. The numbers of animals per treatment group are indicated in the figure.

Figure 4:
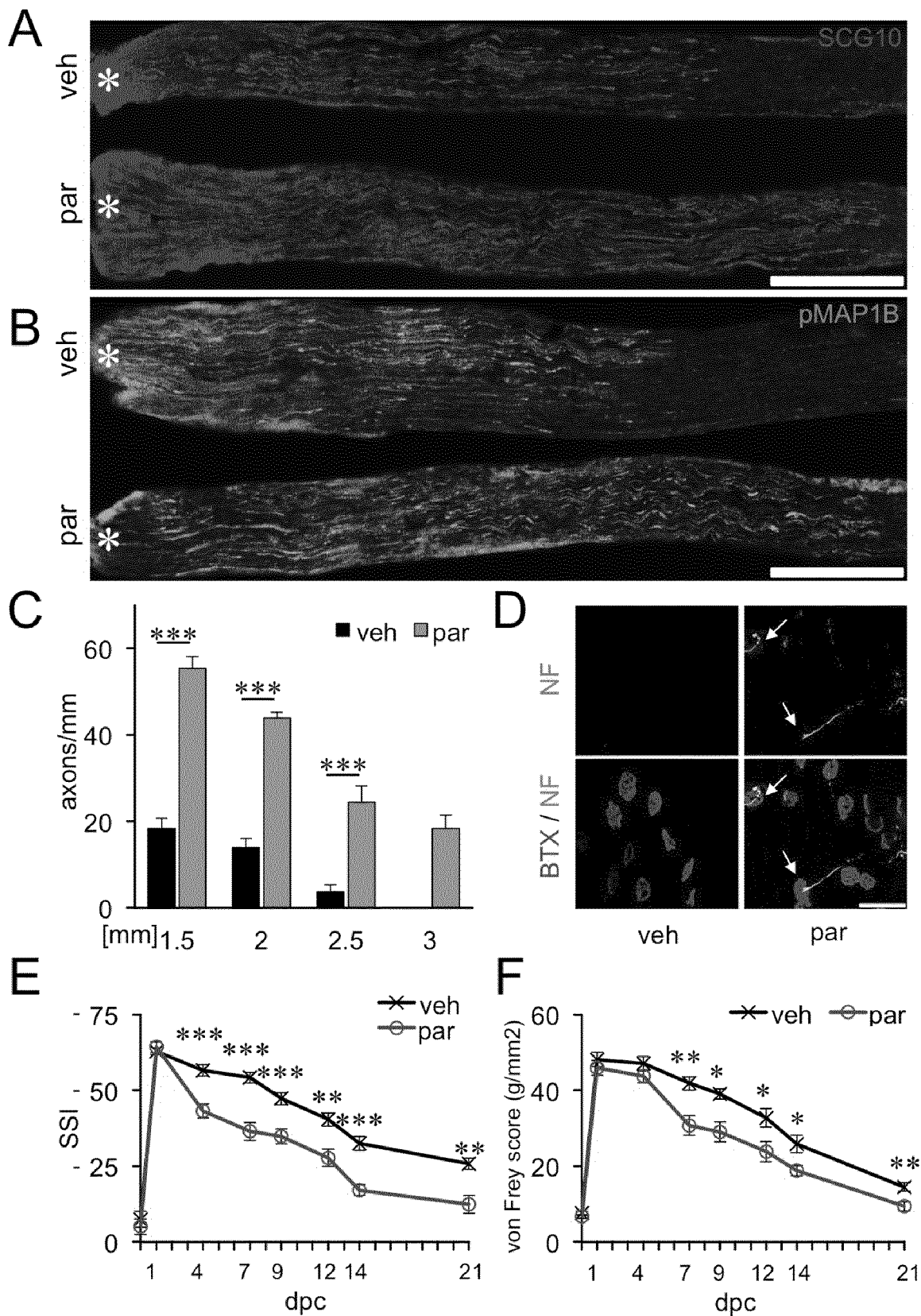

FIG. 4 FIGS. 4A and 4B show longitudinal sections of sciatic nerves 3 days after SNC with either an intraneural injection of vehicle (veh) or 50 nM parthenolide (par). Regenerating axons were immunohistochemically stained for SCG10 FIG. 4A) or pMAP1B (FIG. 4B). Scale bar: 500 μm. Asterisks indicate the crush site. FIG. 4C shows the quantification of axons at >1.5, >2, >2.5 and >3 millimeters beyond the injury site of the sciatic nerve from animals treated either with vehicle (veh) or parthenolide (par) as described in A/B. The error bars represent the standard error of the mean. Statistical significance was determined with ANOVA and the post hoc Holm Sidac test. Treatment effects: *p≤0.001. FIG. 4D shows α-bungarotoxin (BTX) and neurofilament (NF) staining of musculus extensor hallucis longus wholemounts from parthenolide (par) or vehicle treated mice (veh) 4 days after sciatic nerve crush. White arrows indicate reestablished synapses in parthenolide treated mice. Scale bar: 50 μM. FIG. 4E shows the quantification of functional motor recovery determined in adult wild type mice treated with either parthenolide (par, n=11) or vehicle (veh, n=11) by the static sciatic index (SSI) at 1, 4, 7, 9, 12, 14 and 21 days after sciatic nerve crush (dpc). p≤0.01; *p≤0.001. FIG. 4F shows the quantification of sensory functional recovery determined in adult wild type mice treated with either parthenolide (par, n=11) or vehicle (veh, n=11) by the von Frey test at 1, 4, 7, 12, 14 and 21 days after sciatic nerve crush. Treatment effects: p≤0.01; *p≤0.05.

Figure 5:
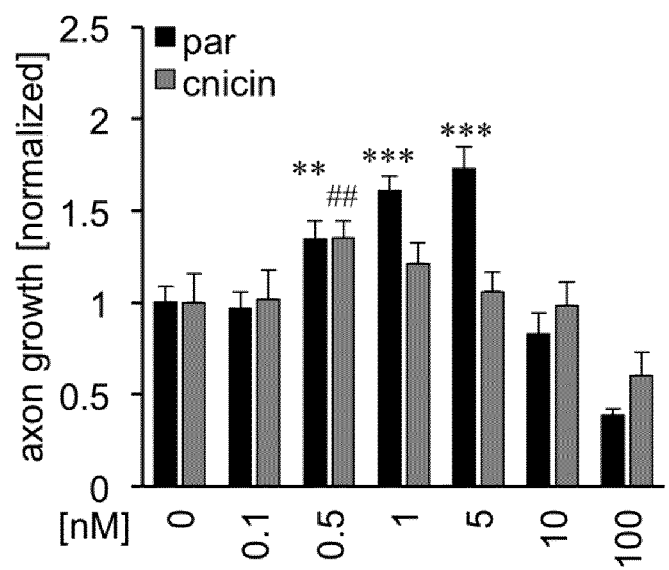

FIG. 5 Quantification of axon growth in wt DRG cultures after treatment with various cnicin and parthenolide (par) concentrations. Data from treated neurons were normalized to vehicle controls with an average axon length of 933 μm/neuron for parthenolide and 546 μm/neuron for cnicin. Data represent means±SEM of three independent experiments. Treatment effects compared to vehicle control: p≤0.01, *p≤0.001, ##p≤0.01, ###p≤0.001.

Figure 6:
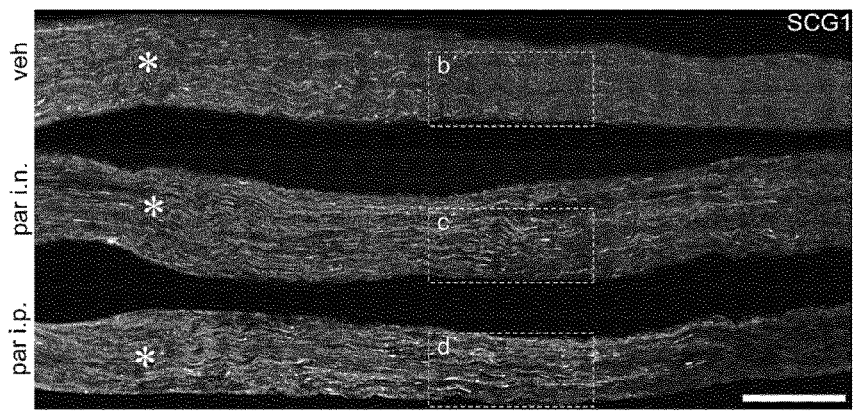
Figure 6:
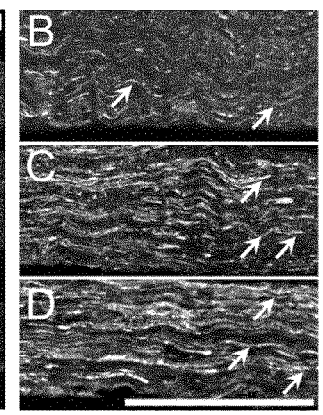
Figure 6:
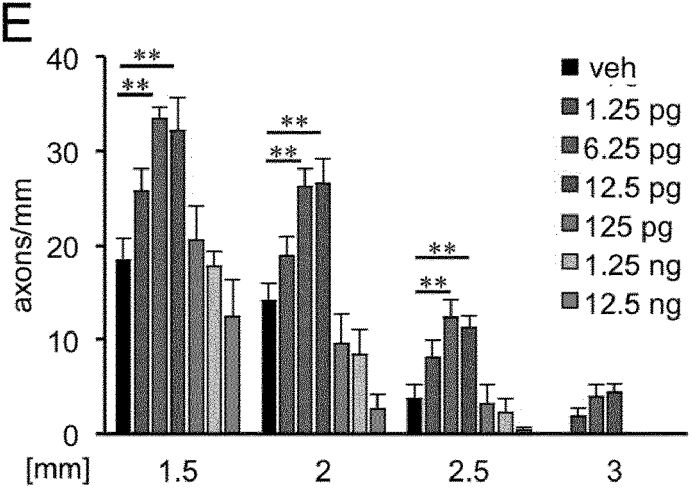
Figure 6:
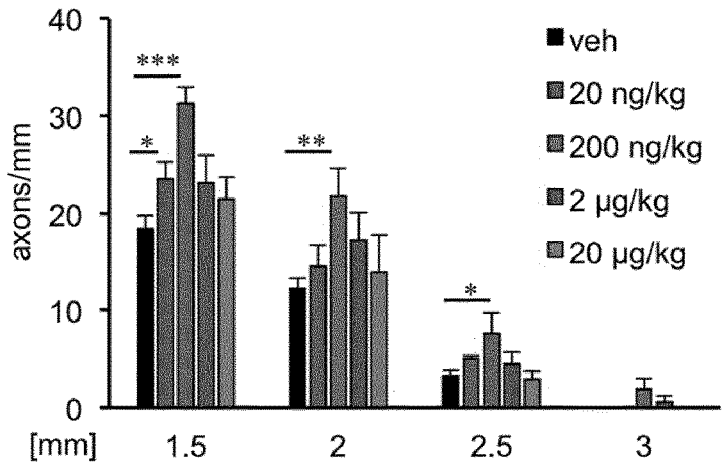

FIG. 6 FIG. 6A) shows representative longitudinal sections of sciatic nerves 3 days after sciatic nerve crush (SNC) and either single intraneural (i.n.) injection of vehicle (top) or parthenolide (6.25 pg par; middle) or intraperitoneal (i.p.) parthenolide injection (200 ng/kg; bottom). Regenerating axons were immunohistochemically stained for SCG10. Scale bar: 500 μm. Asterisks indicate the crush site. FIGS. 6B-D) show magnifications of the respective areas indicated in A. FIGS. 6E, F) show quantification of axons on longitudinal sections at 1.5, 2, 2.5 and 3 millimeters beyond the injury site of sciatic nerves from mice either intraneurally (E) or intraperitoneally (F) injected with vehicle (veh) or various doses of parthenolide (par) as indicated. Data represent means±SEM of five sections from at least six individual mice per experimental group. Treatment effects compared to vehicle injected animals: *p≤0.05, p≤0.01, *p≤0.001.

Figure 7:
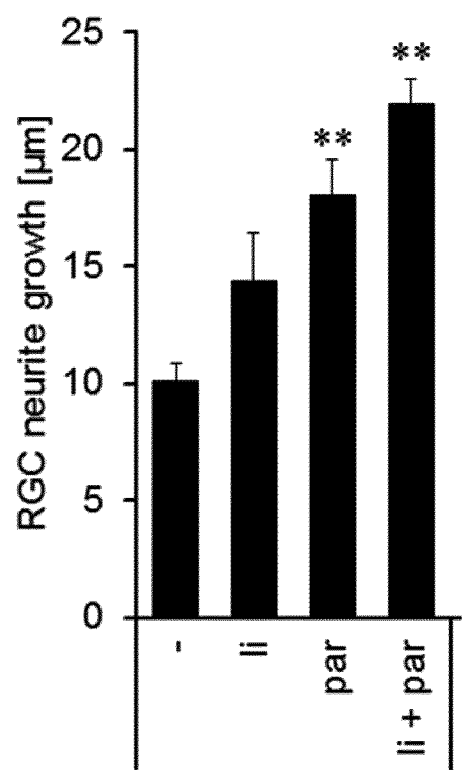

FIG. 7 Quantification of neurite growth of adult retinal ganglion cells after treatment with 1 nM parthenolide (par), lithium (li), or both as indicated. Treatment effects compared to vehicle control ('): **p≤0.01.

EXAMPLES

Materials and Methods:

Parthenolide was purchased from Sigma-Aldrich (St. Louis, Mo.) and dissolved in dimethyl sulfoxide (DMSO) to yield the appropriate concentrations. Nocodazole was purchased from Sigma-Aldrich and dissolved in DMSO to yield the appropriate concentrations. SB216763 was purchased from Sigma-Aldrich and dissolved in DMSO to yield the appropriate concentrations.

Surgical Procedures:

Male and female adult (8-12 weeks) wild type and GSK3α$^{S214}$/GSK3β$^{S9A}$ mice (Prof. Dr. Alessi, University of Dundee) of a C57BL/6,129/Ola genetic background were maintained on a 12-hour light/dark cycle with ad libitum access to food and water and were used for all studies except experiments investigating the effects of parthenolide. Parthenolide experiments were performed with mice of a C57BL/6J background. Animals were housed under the same conditions for at least 10 days prior to use in experiments. Sciatic nerve crush (SNC) was performed as described in Gobrecht et al., Nature communications. 2014; 5:4561. In brief, animals were anesthetized by intraperitoneal injections of ketamine (60-80 mg/kg, Pfizer, New York, US-N.Y.) and xylazine (10-15 mg/kg, Bayer, Leverkusen, Germany). A skin incision of about 10 mm was made over the gluteal region exposing the right sciatic nerve from the sciatic notch to the point of trifurcation. The ischiocrural musculature was carefully spread minimizing tissue damage. The crush injury was performed proximal to the tibial and peroneal divisions for 30 seconds using a Dumont #5 forceps (Hermle, Tuttlingen, Germany) and marked with carbon (Sigma). The skin was closed using 6-0 suture stitches. Injections into the injury site of the sciatic nerve were performed using a microcapillary and Nanoject II™ injector (Drummond Scientific, Broomall, US-Pa.) directly after nerve crush. Five consecutive injections of 69 nl each with a speed of 23 nl/sec and intervals of 30 sec between injections were performed.

DRG Neuron Cultures and Immunocytochemical Staining Procedure:

Dorsal root ganglion (DRG) neurons were isolated from adult wild type (wt) and GSK3α/GSK3β mice as described in Gobrecht et al., Nature communications. 2014; 5:4561. DRGs (T8-L6) were harvested, incubated in 0.25% trypsin/EDTA (GE Healthcare, Chalfont St Giles, UK) and 0.3% collagenase type IA (Sigma, St. Louis, US-Mo.) in DMEM (Life Technologies, Carlsbad, US-Calif.) at 37° C. and 5% $CO_2$ for 45 min and mechanically dissociated. Cells were resuspended in DMEM containing 10% fetal bovine serum (GE Healthcare) penicillin/streptomycin (500 U/ml; Merck Millipore, Billerica, US-MA) and 5-fluoro-2'-desoxyuridine (100 nM; Sigma). Cells were cultured on poly-D-lysine (PDL, 0.1 mg/ml, molecular weight <300,000 kDa; Sigma) and laminin (20 µg/ml; Sigma) coated 96 well plates (Nunc, Germany) at 37° C. and 5% $CO_2$.

For evaluation of MAP1B phosphorylation at threonine 1265 or levels of detyrosinated tubulin in neuronal axon tips, cell cultures were treated with vehicle, 5 µM SB216763 or 1 nM parthenolide and cultured for 3 days. Afterwards, cultures were stained with antibodies against βIII-tubulin (1:2,000; Covance) and pMAP1B (1:1000; Thermo Scientific) or detyrosinated tubulin (1:2000; Millipore). Axon tips were considered to be the last 15 µm of βIII-tubulin positive neuron extensions. Data are presented as the mean±SEM of three replicate wells from at least two separate experiments. Significances of intergroup differences were evaluated using either one- or two-way analysis of variance (ANOVA) followed by Holm-Sidak post hoc test.

Two-Compartment Chamber Cultures:

Two-compartment chambers (AXIS™ Axon Isolation Device, Millipore) were mounted on PDL and laminin coated culture dishes. DRG neurons of adult mice were cultured in the somal compartment for 3 days until neurons extended axons through all microchannels. Neurons were then axotomized by fast removal of medium from the axonal compartment. Afterwards, either parthenolide (5 nM) or vehicle was applied into either the somal or the axonal side. A hydrostatic pressure difference was established between the somal and the axonal chambers to produce a fluid flow preventing diffusion of drugs into microchannels. After another 24 h in culture, neurons were fixed with 4% PFA. The average axon length was quantified after immunocytochemical βIII-tubulin staining.

α-bungarotoxin (BTX) Extensor Hallucis Longus Staining:

In order to analyze the reestablishment of neuromuscular junctions, mice were sacrificed at 4 days after SNC. The extensor hallucis longus muscle was dissected and postfixed in PFA for 1 hour as described in Gobrecht et al., Nature communications. 2014; 5:4561. Afterwards, muscles were permeabilized in 2% TritonX in PBS overnight. Axons where labeled with an antibody against neurofilament (1:2,000; Abcam). Synapses were visualized by incubation with Alexa594-conjugated α-bungarotoxin (BTX) (1:1,000; Invitrogen) in PBS-T for 1 h.

Quantification of Regenerating Axons in Sciatic Nerve Tissue:

Sciatic nerves were isolated, post-fixed for 6 hours, transferred to 30% sucrose overnight at 4° C. and embedded in Tissue-Tek (Sakura, Leiden, Netherlands). Longitudinal and cross-sections were cut on a cryostat (Leica, Wetzlar, Germany), thaw-mounted onto coated glass slides (Superfrost plus, Fisher, Pittsburgh, US-Pa.) and stored at −20° C. for further use. Cryosections (14 µm) of sciatic nerves were immunohistochemically stained with an antibody against the regeneration-associated protein SCG10 (1:1,500; Novus Biologicals, Cambridge, UK) or against pMAP1B (1:500; Thermo Scientific). SCG10-positive axons were quantified at various points beyond the carbon-labeled injury site, as described in Gobrecht et al., Nature communications. 2014; 5:4561. Statistical significances of intergroup differences were evaluated using a one-way ANOVA followed by the Holm-Sidak post hoc test. Each experimental group included at least five sections from five mice.

Static Sciatic Index:

Functional functional motor recovery was quantified in 11 C57BL/6J mice with intraneural injections of vehicle and 11 animals with parthenolide treatment by calculating the static sciatic index (SSI) as described in Baptista A F et al., J Neurosci Methods. 2007; 161(2):259-64.

Mice were lifted from the ground to photograph the left and right hind feet, respectively. Toe spreading on the contra—(C, left) and ipsilateral (I, right) sides of the sciatic nerve crush was assessed in wild-type and transgenic GSK3 knockin mice at 0, 1, 4, 7, 9, 11, 14, 17 and 21 days after SNC by measuring the paw length (PL) and the distance between the first and the fifth toe (FF). The static sciatic index SSI was calculated based on the previously described formula: SSI=101.3 ((IFF−CFF)/CFF)−54.03((IPL-CPL)/CPL)−9.5 as described in Baptista A F et al., J Neurosci Methods. 2007; 161(2):259-64.

Data are represented as mean and ±SEM from 8-10 animals per experimental group.

Statistical significances of intergroup differences were evaluated using a two-way ANOVA followed by the Holm-Sidak post hoc test.

Von Frey Test:

Functional sensory recovery after SNC was determined with the von Frey filament test as described in Gobrecht et al., Nature communications. 2014; 5:4561 at 0, 1, 4, 7, 14 and 21 days after SNC in 11 animals per experimental group. The test was performed at the same time of the day and by the same experimenter.

To this end, mice were placed on an elevated metal grid (grid size: 2 mm) and allowed to acclimate for 15 minutes before testing. Then, responses of the ipsilateral hind paw to a range of innocuous von Frey filaments (Muromachi Kikai Co., LTD, Tokyo, Japan) were considered, starting with the smallest filament and increasing filament size until a positive response was initiated, which is indicated by a sharp withdrawal of the paw. Statistical significances of intergroup differences were evaluated using a two-way ANOVA followed by the Holm-Sidak post hoc test.

Example 1: Axonal Regeneration Via Inhibition of Tubulin Carboxypeptidase in Axonal Tips by Parthenolide In Vitro 1.1 Determination of Axonal Growth in Culture The effect of the tubulin carboxypeptidase (TCP) inhibitor parthenolide on axon growth of mature neurons was determined in dissociated DRG neurons from adult wild type mice as described above. The cells were treated with vehicle, 0.1 nM, 1 nM, 2.5 nM, 5 nM, 10 nM or 100 nM parthenolide and cultured for 2 days.

The FIG. 1A shows the cells treated with vehicle, 1 nM, 10 nM and 100 nM parthenolide and stained with βIII-tubulin after 2 days in culture. The FIG. 1B shows the quantification of axon growth of the neuronal cultures. Data from three independent experiments were normalized to the vehicle treated control group with an average axon length of 933 μm/neuron. As can be taken from FIGS. 1A and 1B, parthenolide significantly and concentration-dependently increased axon growth. Strongest effects were measured at 1 nM to 5 nM, whereas concentrations ≥100 nM reduced axon growth in culture. This demonstrates that the effect of parthenolide was concentration dependent.

1.2 Determination of Modulation of Microtubule Dynamics

To verify that axon growth affected by parthenolide was mediated via modulation of microtubule dynamics, the effect of parthenolide was evaluated against Glycogen synthase kinase 3 (GSK3) inhibitor SB216763 (sb) and nocodazole (noco) which are known to destabilize microtubules and reduced axon growth.

Glycogen synthase kinase 3 (GSK3) is a protein kinase comprising two isoforms (GSK3α and GSK3β). Both isoforms are phosphorylated and inactivated via phosphatidylinositide 3-kinase (PI3K)/AKT signaling upon sciatic nerve crush (SNC). In GSK3α/GSK3β double knock-in mice (GSK3$^{S/A}$) wherein serine 21 of GSK3a and serine 9 of GSK3β are substituted by alanine, inhibitory GSK3 phosphorylation by AKT is prevented, thereby rendering GSK3 constitutively active. Sustained GSK3 activity markedly accelerates axon regeneration after sciatic nerve crush. These effects are associated with elevated MAP1B phosphorylation.

Dissociated DRG neurons from adult wild type mice and GSK3α/GSK3β double knock-in mice (α/β) were each treated with vehicle (veh), 1 nM parthenolide, 5 μM GSK3 inhibitor SB216763 (sb), 1 nM parthenolide (par), a combination of 5 μM sb and 1 nM par, 10 nM nocodazole (noco) or a combination of par+noco and cultured for 2 days. The FIG. 1C shows the quantification of the respective axon growth after 2 days in culture. As can be taken from the FIG. 1C, the beneficial effects of parthenolide were not affected by SB216763, which, however, efficiently blocked GSK3α$^{S/}$$_A$/GSK3β$^{S/A}$ promoted axon growth. In comparison, nocodazole abrogated the beneficial effects of both GSK3α$^{S/A}$/GSK3β$^{S/A}$ and parthenolide to similar extent, suggesting that parthenolide as well as GSK3α$^{S/A}$/GSK3β$^{S/A}$ increase the susceptibility towards microtubule-disrupting agents.

This finding demonstrates that the positive effect of parthenolide on axon regeneration was likely mediated via modulation of microtubule dynamics.

1.3 Determination of Parthenolide Interaction with Existing Axons

To verify that parthenolide directly interacted with existing axons rather than initiating axon formation in cultures and that it is also sufficient to promote axon regeneration of already growth-stimulated DRG neurons two-compartment culture platforms that permit fluidic isolation of somal and axonal compartments as described above were utilized. To this end adult DRG neurons were cultured in two-compartment chambers for 3 days, so that they were in a regenerative state and then axotomized 1 day after axotomy vehicle (veh) or 5 nM parthenolide were either applied into the somal (par, soma) or in the axonal compartments (par, axon) while the other compartment received vehicle, respectively. Control cells received vehicle into each compartment.

FIG. 1D shows the βIII-tubulin-positive axons of the adult DRG neurons growing through microchannels of two-compartment chambers. FIG. 1E shows the quantification of axon growth 1 day after axotomy. Data from 5 experiments were averaged. As can be taken from FIG. 1E, while parthenolide in the somal chamber did not raise axon growth above vehicle treated levels, parthenolide in the axonal chamber significantly increased axon regeneration. This demonstrates that the length of existing axons was increased by parthenolide.

These observations indicate that moderate pharmacological TCP inhibition by parthenolide increases the dynamicity of microtubules and leads to axon growth promotion in cultured neurons.

Example 2: Determination that Parthenolide Effected Detyrosination of Microtubules In Vitro To verify that parthenolide effected axon growth of mature neurons was promoted via inhibition of microtubule detyrosination, axonal tips of cultured DRG neurons from wild type (wt) or GSK3S/A double knock-in mice (α/β) were either exposed to vehicle (−) or 5 μM GSK3 inhibitor SB216763 (sb) or 10 nM parthenolide (par). Three days after exposure axons were stained for detyrosinated tubulin and βIII-tubulin. It was seen that parthenolide treatment reduced levels of detyrosinated tubulin in axonal tips. FIG. 2 shows the quantification of non-detyrosinated tubulin-positive axon tips of cultures from wt and GSK3S/A double knock-in mice (α/β) 3 days after exposure to vehicle (−), 5 μM SB216763 (sb) or 10 nM parthenolide (par). Data from three independent experiments were normalized to the vehicle treated wt group. As can be taken from FIG. 2, parthenolide increased the percentage of non-detyrosinated axonal tips in adult wild-type neurons significantly and to a similar extent as measured in GSK3α$^{S/A}$/GSK3β$^{S/A}$ neurons.

This indicates that parthenolide effected axon growth of mature neurons is promoted via inhibition of microtubule detyrosination.

Example 3: Determination of Concentration Dependency of Parthenolide Effect on Sciatic Nerve Regeneration In Vivo Increasing concentrations of 0.01 μM, 0.05 μM, 0.1 μM, 1 μM, 10 μM and 100 μM parthenolide were applied into the crush site of sciatic nerves of wild-type mice immediately after sciatic nerve injury, and axon regeneration in sciatic nerve sections was evaluated to determine concentration effects. Three days after sciatic nerve crush and treatment sciatic nerves were isolated, and stained with an antibody against the regeneration-associated protein SCG10. SCG10-positive axons were quantified at 2 mm and 3 mm beyond the carbon-labeled injury site. For the vehicle and 0.05 μM parthenolide group five animals were used per group, for the other concentrations two animals each. Five sciatic nerve sections were analyzed per animal.

FIG. 3 shows the quantification of axon regeneration into the sciatic nerve 3 days after sciatic nerve crush after treatment with vehicle (veh) or the various parthenolide concentrations. As can be taken from the FIG. 3, concentrations ranging from 0.01 μM to 0.1 μM markedly and similarly increased axon regeneration in the injured sciatic nerve 3 days after SNC, while higher concentrations above 10 μM rather reduced it.

Example 4: Intraneural Parthenolide Application In Vivo

4.1 Determination of Sciatic Nerve Regeneration In Vivo

To investigate if intraneural application of parthenolide promotes sciatic nerve regeneration in vivo either 50 nM of parthenolide or vehicle were applied into the crushed sciatic nerve of wild-type mice simultaneously with surgery and the effect on regeneration was determined 3 days after SNC.

FIGS. 4A and 4B show longitudinal sections of sciatic nerves 3 days after SNC with either an intraneural injection of vehicle (veh) or 50 nM parthenolide (par). Regenerating axons were immunohistochemically stained for SCG10 as shown in FIG. 4A or pMAP1B as shown in FIG. 4B. As can be taken from FIGS. 4A and 4B, parthenolide treatment enabled axons to regenerate over longer distances beyond the injury site without elevating axonal pMAP1B levels. FIG. 4C shows the quantification of axons at >1.5 mm, >2 mm, >2.5 mm and >3 millimeters beyond the injury site of the sciatic nerve from animals treated either with vehicle (veh) or parthenolide (par) as described. As can be seen in FIG. 4C, parthenolide application markedly increased the number of axons at a distance of 2.5 mm beyond the lesion site >6-fold compared to vehicle treated controls. Axons at distances of 3 mm past the injury site were only observed after treatment with parthenolide 3 days after surgery.

This finding shows that one single injection was sufficient to significantly accelerate functional regeneration compared to vehicle treated controls. It is assumed that repeated intraneural injections of the TCP inhibitor or systemic application of the drug can further accelerate axon regeneration. Further, axon regeneration promoting effect of parthenolide was stronger compared with GSK3α$^{S/A}$/GSK3β$^{S/A}$ knock-in animals and not associated with increased MAP1B phosphorylation.

4.2 Determination of reestablishment of neuromuscular junctions after parthenolide treatment To verify that regenerating axons had already started to successfully reinnervate their targets 4 days after parthenolide treatment a BTX and neurofilament staining of the musculus extensor hallucis longus was performed. Mice were sacrificed at 4 days after SNC and treatment with 50 nM parthenolide (par), and the extensor hallucis longus muscle was dissected and stained. FIG. 4D shows the α-bungarotoxin (BTX) and neurofilament (NF) staining of musculus extensor hallucis longus wholemounts from parthenolide (par) or vehicle treated mice (veh) 4 days after sciatic nerve crush. As indicated in FIG. 4D neuromuscular junctions were found in parthenolide treated animals, but not in vehicle treated controls.

4.3 Determination of Functional Recovery

To test whether parthenolide application also accelerated functional recovery in vivo, the regenerative outcome of adult wild type mice after treatment with 50 nM parthenolide after sciatic nerve crush was functionally assessed using the static sciatic index (SSI) and the von Frey tests as described above.

FIG. 4E shows the quantification of functional motor recovery determined in adult wild type mice treated with either parthenolide (par, n=11) or vehicle (veh, n=11) by the static sciatic index (SSI) at 1, 4, 7, 9, 12, 14 and 21 days after sciatic nerve crush (dpc). As can be seen in FIG. 4E, parthenolide treated animals showed already a significantly improved SSI score at 4 days after injury compared to vehicle treated control animals, which was sustained over the total observation period of 3 weeks.

FIG. 4F shows the quantification of sensory functional recovery determined in adult wild type mice treated with either parthenolide (par, n=11) or vehicle (veh, n=11) by the von Frey test at 1, 4, 7, 12, 14 and 21 days after sciatic nerve crush. As can be seen in FIG. 4F, parthenolide treatment also accelerated sensory recovery. First improvements were detectable in the von Frey test at 7 days after injury and still significant at 12 and 14 days, thereby reflecting the longer distances required for axons to reach their respective targets for sensory recovery.

These data demonstrate that intraneural application of parthenolide markedly promotes sciatic nerve regeneration and accelerates functional motor and sensory recovery in vivo.

Example 5: Determination of Axonal Growth In Vitro after Application of Parthenolide and Cnicin Dorsal root ganglion (DRG) neurons were isolated from adult wild type (wt) and GSK3α/GSK3βmice as described in Gobrecht et al., Nature communications. 2014; 5:4561. DRGs (T8-L6) were harvested, incubated in 0.25% trypsin/EDTA (GE Healthcare, Chalfont St Giles, UK) and 0.3% collagenase type IA (Sigma, St. Louis, US-Mo.) in DMEM (Life Technologies, Carlsbad, US-Calif.) at 37° C. and 5% $CO_2$ for 45 min and mechanically dissociated. Cells were resuspended in DMEM containing 10% fetal bovine serum (GE Healthcare) penicillin/streptomycin (500 U/ml; Merck Millipore, Billerica, US-Mass.) and 5-fluoro-2'-desoxyuridine (100 nM; Sigma). Cells were cultured on poly-D-lysine (PDL, 0.1 mg/ml, molecular weight <300,000 kDa; Sigma) and laminin (20 µg/ml; Sigma) coated 96 well plates (Nunc, Germany) at 37° C. and 5% $CO_2$. Cells were treated with vehicle, or either 0.1 nM, 0.5 nM, 1 nM, 5 nM, 10 nM or 100 nM parthenolide (Sigma-Aldrich) or cnicin (Extrasynthese) and cultured for 2 days.

Axonal growth was determined upon 48 h incubation by fixation in 4% PFA (Sigma) and immunocytochemical staining with antibodies against NeuN (1:2,000; Abcam, ab177487, Cambridge, UK) and βIII-tubulin (1:2,000; Covance, Princeton, US-N.J.). Imaging and quantification of total axon length and neuron numbers per well were automatically performed with the Pathway 855 microscope system (BD, Franklin Lakes, US-N.J.) and Attovision software, avoiding experimenter-induced quantification bias. Average axon length per neuron and neuron counts per experimental group were normalized to control groups.

FIG. 5 shows the quantification of axon growth of the neuronal cultures. Data represent means±SEM of at least six replicate wells per experiment and three independent experiments. Significances of intergroup differences were evaluated using either one- or two-way analysis of variance (ANOVA) followed by the Holm-Sidak post hoc test. As can be taken from FIG. 5, parthenolide significantly and concentration-dependently increased axon growth. Strongest effects were measured at 1 nM and 5 nM, whereas concentrations ≥100 nM reduced axon growth in culture. This demonstrates that the effect of parthenolide was concentration dependent. As cell numbers remained unaffected for all tested concentrations, general toxicity was not observed. In comparison to parthenolide, the derivate cnicin showed also significant, but less pronounced axon growth promotion with strongest effects at 0.5 nM.

Example 6: Determination of Sciatic Nerve Regeneration In Vivo after Intraneural and Systemic Application of Parthenolide

6.1: Intraneural Parthenolide Application

As described in Example 4.1, doses of 1.25 pg, 6.25 pg, 12.5 pg, 125 pg, 1,250 pg and 12,500 pg parthenolide were applied into the crush site of sciatic nerves of wild-type mice simultaneously with surgery and the effect on regeneration was determined 3 days later.

FIGS. 6A, B and C show longitudinal sections of sciatic nerves 3 days after sciatic nerve crush (SNC) and either single intraneural (i.n.) injection of vehicle (top) or parthenolide (6.25 pg par; middle). FIGS. 6B and C show magnifications of the respective areas indicated in A. As can be taken from FIGS. 6A, B and C, only few axonal profiles were detected at ~2.5 mm past the lesion in vehicle injected animals (B), while significantly more regenerating axons were present after intraneural (C) parthenolide injection. FIG. 6E shows the quantification of axons on longitudinal sections at 1.5 mm, 2 mm, 2.5 mm and 3 millimeters beyond the injury site of sciatic nerves from mice intraneurally injected with vehicle (veh) or parthenolide. As can be taken from FIG. 6E, intraneurally applied doses ranging from 1.25 to 12.5 pg markedly increased axon regeneration 3 days after SNC. Strongest growth promotion was determined at doses of 6.25 pg and 12.5 pg, which increased the number of axons more than 3-fold compared to vehicle-treated controls at a distance of 2.5 mm beyond the lesion site.

6.2: Systemic Application of Parthenolide

To test whether systemic parthenolide administration is able to promote sciatic nerve regeneration, parthenolide doses of 20 ng/kg, 200 ng/kg, 2 µg/kg, and 20 µg/kg were injected intraperitoneally after sciatic nerve injury.

FIGS. 6A and D shows longitudinal sections of sciatic nerves 3 days after sciatic nerve crush (SNC) and intraperitoneal (i.p.) parthenolide injection (200 ng/kg; bottom). FIG. 6D shows a magnification of the respective area after intraperitoneal (i.p.) parthenolide injection indicated in A. As can be taken from FIGS. 6A and D, also significantly more regenerating axons were present after intraperitoneal (D) parthenolide injection. FIG. 6F shows quantification of axons on longitudinal sections at 1.5 mm, 2 mm, 2.5 mm and 3 mm beyond the injury site of sciatic nerves intraperitoneally injected with vehicle (veh) or parthenolide. As can be taken from FIG. 6F, a single injection of 200 ng/kg significantly increased the number of regenerating axons ~2.5-fold at 2.5 mm, which is slightly less pronounced compared to intraneural parthenolide application. Higher tested doses did not significantly affect sciatic nerve regeneration.

These data demonstrate that also systemic application of parthenolide markedly promotes sciatic nerve regeneration and accelerates functional motor and sensory recovery in vivo.

Example 7: Determination of the Effect of Parthenolide on Cells of the Central Nervous System To test whether parthenolide is effective on cells of the central nervous system, neurite outgrowth of adult retinal ganglion cells was determined. To this end adult murine retinae were dissociated and cultured for 4 days either in the presence of vehicle (−), lithium (li) or parthenolide (Par, 1 nM). Cells were fixed and stained for betaIII tubulin and neurite length per retinal ganglion cell determined. The quantification of neurite growth of the retinal ganglion cells after treatment with 1 nM parthenolide (par), lithium (li), or both as shown in FIG. 7. As can be taken from FIG. 7, parthenolide markedly and significantly promoted neurite growth compared to untreated controls. Lithium showed no significant effect, but further enhanced the beneficial effect of parthenolide.

These data demonstrate that parthenolide not only is able to promote nerve regeneration of peripheral nerves such as of the sciatic nerve, but also of central neurons. This finding suggests that parthenolide might be also useful to promote CNS regeneration, such as after injuries in the optic nerve or spinal cord.

Together these data provide a novel therapeutic approach to promote nerve regeneration and for treatment of nerve injury. It was shown that inhibition of microtubule detyrosination in growth cones in the injured nerve by pharmacological TCP inhibition in vivo using parthenolide provides a novel and clinically feasible approach to accelerate axon regeneration and to improve functional recovery.

The invention claimed is:

1. A method of regenerating axonal damage, wherein the axonal damage is an injury of the sciatic nerve, the method comprising administering to a subject a therapeutically effective amount of a compound reducing microtubule detyrosination in axonal tips selected from cnicin or a pharmaceutically acceptable salt thereof.

2. A method of regenerating axonal damage, wherein the axonal damage is an axotomy of the sciatic nerve, the method comprising administering to a subject a therapeutically effective amount of a compound reducing microtubule detyrosination in axonal tips selected from cnicin or a pharmaceutically acceptable salt thereof.

* * * * *